United States Patent [19]

Foran

[11] Patent Number: 4,767,407
[45] Date of Patent: Aug. 30, 1988

[54] HYPODERMIC NEEDLE, CATHETER AND METHOD

[76] Inventor: Scot J. Foran, 246 S. Maple, #3W, Oak Park, Ill. 60302

[21] Appl. No.: 885,430

[22] Filed: Jul. 14, 1986

[51] Int. Cl.⁴ ............................................. A61M 5/18
[52] U.S. Cl. ................................... 604/164; 604/117; 604/239; 604/272
[58] Field of Search ............... 604/117, 164, 239, 240, 604/243, 244, 264, 272, 273, 274, 168, 158

[56] References Cited

U.S. PATENT DOCUMENTS

| | | | |
|---|---|---|---|
| 422,436 | 3/1890 | Otto | 604/273 |
| 600,803 | 3/1898 | Robinson et al. | 604/273 |
| 1,100,181 | 6/1914 | Hart | 604/272 |
| 1,648,308 | 11/1927 | Hofschneider | 604/243 |
| 2,541,542 | 2/1951 | Perez . | |
| 2,716,983 | 9/1955 | Windischman et al. | 604/274 |
| 2,725,058 | 11/1955 | Rathkey | 604/272 |
| 2,904,045 | 4/1958 | Owings | 604/274 |
| 3,216,616 | 11/1965 | Blankenship, Jr. . | |
| 3,540,447 | 11/1970 | Howe . | |
| 3,662,754 | 5/1972 | Halloran . | |
| 3,993,079 | 11/1976 | Gatztanondo . | |
| 4,193,400 | 3/1980 | Loveless . | |
| 4,317,445 | 3/1982 | Robinson . | |
| 4,335,718 | 6/1982 | Calabrese . | |
| 4,490,136 | 12/1984 | Ekbladh et al. | 604/272 |
| 4,512,766 | 4/1985 | Vailandcourt | 604/256 |
| 4,565,545 | 1/1986 | Suzuki . | |
| 4,588,398 | 5/1986 | Daugherty . | |

FOREIGN PATENT DOCUMENTS

| | | | |
|---|---|---|---|
| 2481159 | 10/1981 | France | 604/272 |
| 2481930 | 11/1981 | France | 604/239 |

Primary Examiner—Stephen C. Pellegrino
Assistant Examiner—Ralph Lewis
Attorney, Agent, or Firm—James T. FitzGibbon

[57] ABSTRACT

A hypodermic needle assembly is provided for intravenous use, such being for positioning a catheter into a vein. The needle assembly includes a lumen having more than one diameter which is provided in association with a tip structure having multiple beveled surfaces in order to provide a needle assembly that is especially suitable for use with patients who are elderly or in ill health or who have venous construction or collapse due to trauma or the like.

12 Claims, 2 Drawing Sheets

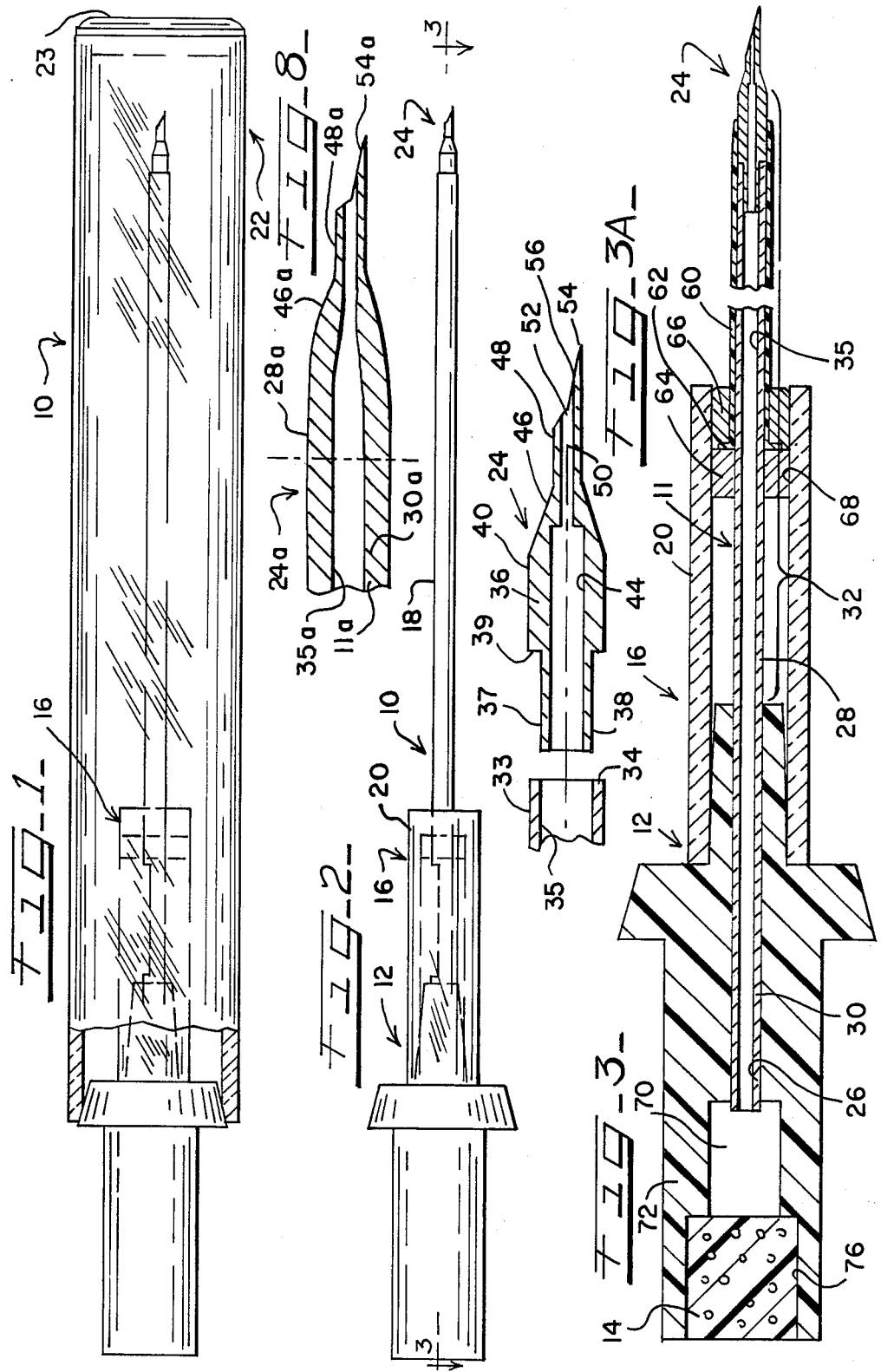

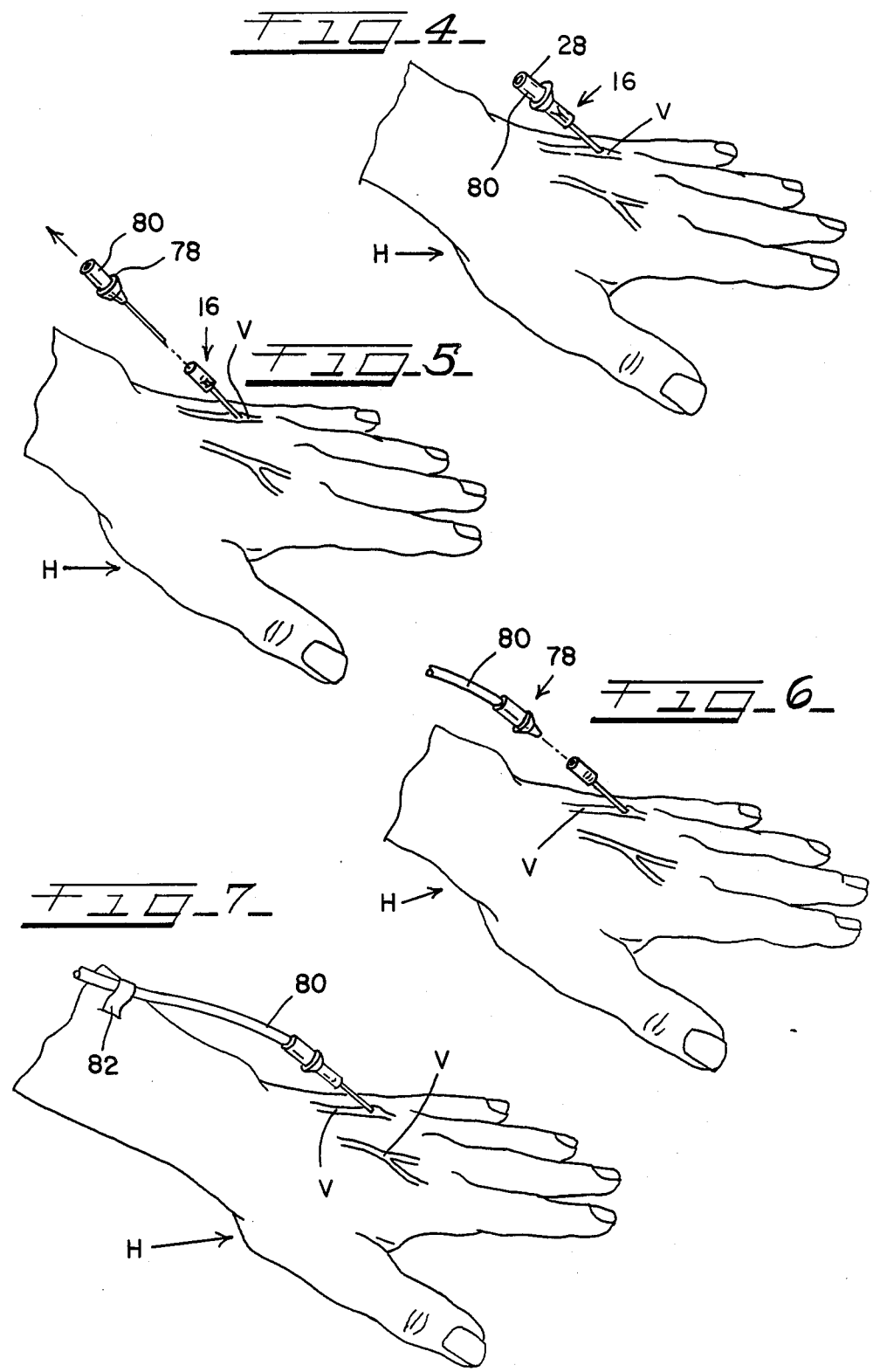

HYPODERMIC NEEDLE, CATHETER AND METHOD

The present invention relates generally to an improved hypodermic needle, and more particularly, to an improved apparatus for administration of intravenous fluids to the body, particularly under conditions previously throught to create difficulty in such administration.

According to present practice, intravenous fluids of many kinds are administered to patients by co-called percutaneous injection, that is, piercing the skin with a hollow needle inserted into the vein in the hand, arm, or elsewhere in the patient. A generally standardized system of intravenous tubes, connectors and needles has been manufactured and is commonly accepted by the medical community for this purpose. Under common conditions of use, existing systems are satisfactory; however, like other engineered systems and products, they are still capable of further improvement. Moreover, there are certain circumstances in which existing needles used for intravenous administration of medicines and other fluids are inadequate or disadvantageous.

Referring to a common situation, following serious injury, it may be desired to administer fluid to a patient intravenously. However, because of the nature of the injury, and the condition and/or the position of the patient, it is difficult to locate the veins or to pierce the vein in such a way that the needle is inserted fully into, but does not pass through the vein. For this purpose, most needles have simply been too large and unwieldly, and hence, incapable of reliable insertion into veins, especially those which are constricted or collapsed, as is often the case following trauma or other medical emergency.

According to the present invention, a combination needle and catheter system is provided for use by medical personnel, especially members of an emergency medical team. The combination includes a needle having a greatly reduced diameter insertion end portion provided either by a separately manufactured, but permanently affixed tip, or as an integral portion of the needle itself.

The present invention thus concerns needles for intravenous administration of fluids which needles each include a shank or cannula portion and a tip portion having a reduced diameter gauge portion proximate to the tip bevel to facilitate ready venipuncture, this is, ready insertion.

In view of the failure of the prior art to provide needles and insertion systems of the type described, it is an object of the present invention to provide an improved needle for intravenous administration of fluids.

A further object of the invention is to provide an improved intravenous needle which is adapted for connection with existing intravenous feed tubes and other apparatus which are readily available.

Another object of the invention is to provide a needle of improved design and overall performance, which can be manufactured by known techniques under controlled conditions and at moderate cost using existing technology.

Yet another object of the invention is to provide a needle having a novel, separately manufactured tip assembly.

A still further object of the invention is to provide a combination needle and catheter assembly wherein the needle includes a reduced diameter gauge section, and includes, in addition to a tip bevel, a forward or proximal gauge section of reduced diameter, a tapered or remote tip body bevel portion and an exterior tip body having a gauge portion of enlarged diameter, with a central passage being provided therethrough for fluid flow.

Another object of the invention is to provide a novel method of manufacturing a needle assembly which includes making a needle body having a proximate end for reception of a novel tip, a remote end for insertion into a needle hub, an intermediate or cannula portion for positioning an indwelling catheter, and a novel tip which has a body with a reduced gauge proximate end terminating in a pointed tip and a remote end received within said needle body.

Another object of the invention is to provide a combination needle and an indwelling catheter assembly capable of improved reliablity and safety in use.

The foregoing and other objects and advantages of the invention are achieved in practice by providing a needle having a needle body, including a cannula portion, proximal end and a remote end, and a needle tip portion which includes an outer gauge portion of the same diameter as the cannula, and a proximal or forward end portion of substantially reduced gauge, with the needle terminating in a forward tip and bevel portion, and including an axially extending tip lumen to provide communication with the lumen in the interior of said needle body.

The manner in which the foregoing and other objects and advantages of the invention are achieved in practice will become more clearly apparent when reference is made to the following detailed description of the preferred embodiments of the invention set forth by way of example and shown in the accompanying drawings where like reference numbers indicate corresponding parts throughout.

BRIEF DESCRIPTION OF THE DRAWINGS

FIG. 1 is a side elevational view, with a portion broken away, showing the novel hypodermic needle, catheter, and protective cover assembly of the present invention before use thereof;

FIG. 2 is a side elevation view showing the needle and catheter of the invention with the protective cover removed;

FIG. 3 is a vertical sectional view, with a portion broken away, and taken on an enlarged scale and showing the elements of the needle, catheter, needle hub, needle tip assembly greater detail;

FIG. 3A is a vertical sectional view on a further enlarged scale showing the novel needle tip assembly of the present invention just prior to assembly with the needle tube;

FIG. 4 is a perspective view showing initial insertion of the needle and catheter assembly of the invention in the hand of a human patient;

FIG. 5 is a perspective view similar to that of FIG. 4 and showing the removal of the needle from the catheter to expose the distal end of the catheter assembly;

FIG. 6 is a view similar to that of FIGS. 4 and 5 and showing a standard intravenous tubing and male coupler unit just prior to assembly with the female coupler forming the distal end portion of the catheter;

FIG. 7 is a view similar to that of FIGS. 4–6 and showing the catheter in place in the patient with the intravenous feeding liquid supply tube also in place on the hand of the patient; and FIG. 8 is an enlarged fragmentary vertical sectional view of a modified form of needle made according to the invention.

DESCRIPTION OF THE PREFERRED EMBODIMENTS OF THE INVENTION

While the invention is capable of different applications, and may be embodied in different forms, a detailed description thereof will be given of one form of needle wherein the needle itself is made from a stainless steel material and includes a novel stainless steel tip assembly, wherein the needle is covered in use by a fluorocarbon resin indwelling catheter having a female coupler forming one end portion thereof, and wherein the metal portions of the intravenous needle are assembled by silver soldering or the like. In another form, a unitary needle is shown and described.

Referring now to the drawings in greater detail, FIGS. 1-3 show the invention to be embodied in a novel needle and tip assembly generally designated 10 and shown to include a tubular needle body generally designated 11, a needle hub assembly generally designated 12, a hub plug 14, a catheter and half coupler assembly generally designated 16 which includes a catheter 18 and a half coupler 20, with the forward portion of the entire assembly 10 being received in a protective sheath or tube generally designated 22 and shown to have a closed end 23.

According to the invention, a novel needle tip assembly generally designated 24 in FIGS. 2, 3, and 3A is shown to serve as the proximal or forward end of the entire needle assembly 10. In this specification, and in the claims, "proximal" or words of like import denote the portion toward the needle tip and proximal of the patient when the needle is in use, while "distal", "remote", or like words refer to the portions of the assembly which are remote from the region of percutaneous needle insertion.

Referring now to FIGS. 3 and 3A, other elements of the invention are shown in detail, bearing in mind that the invention is directed primarily to the needle having a novel tip assembly which may be manufactured in separate components for subsequent assembly, or may be formed as a single unit.

According to the invention, the needle hub 21 includes an inner diameter, axially extending center bore 26 adapted to receive the outer diameter or gauge surface portion 28 of the distal end portion 30 of the hypodermic needle body 11. The exposed or cannula portion 32 of the needle also includes a gauge surface 28 of the same diameter; the cannular terminates at its forward or proximal end 33 in an end face surface portion 34. The needle body 11 includes its own cylindrical passage or lumen 35 which is of a constant diameter throughout the entire cylindrical needle body 11.

According to the invention, a novel tip assembly generally designated 24 is shown to include a number of elements including a cylindrical tip body 36, a tip body rear extension portion 37, having a distal or remote gauge portion 38, a radially extending tip shoulder 39, and a tip body gauge surface 40. Extending generally concentrically of these surfaces and axially within the principal portions of the tip body 36 and rear extension 37 is a major or enlarged diameter lumen 44.

The tip assembly further includes a remote or exterior body bevel portion 46 of frustoconical configuration and terminating at its proximal or forward end in a proximal or exposed tip gauge section 48. This tip gauge section 48 has a minor or reduced diameter lumen 50 running throughout its entire extent, with the major and minor diameter lumens 44, 50 communicating with each other within the tip body 36.

The forward end of the proximal tip gauge section 48 includes a tip heel portion 52 and a forwardmost pointed end portion 54. The tip and heel 54, 52 are connected by a proximal tip bevel 56, which bevel may be of the so-called triple bevel construction known to those skilled in the hypodermic needle art.

According to the invention, the tip assembly 24 just described is assembled with the needle body 11 by press fitting and silver soldering the gauge section 38 of the tip extension 37 to the inner diameter surface 35 of the needle body 11. In carrying out this assembly, there is an interference or just less than an interference fit between the gauge portion 38 of the rear body extension 37 and the surface 35. In this construction, the tip body shoulder 39 and the needle sleeve end surface portion 34 are in abutting relation. As a consequence of this construction, the passages or lumens of the needle interior comprise three different diameters, the smallest and the intermediate diameters 50, 44, respectively, being those provided in the needle tip 24, and the largest being that of the lumen 35 in the needle body 11.

Referring now to the catheter 18, this is of conventional construction and includes a tubular sleeve portion 60 terminating at its inner end in a radial flange 62 received in fluid-tight relation between axially inner and outer annular stub sleeves 64, 66. These elements 64, 66 are in turn disposed such that their outer diameters sealingly engage the inner surface 68 of the I.V. half coupler 20 in fluid-tight relation.

FIGS. 4 through 7 show the use of the needle of the invention in making a venipuncture on a patient whose hand H is generally shown in FIGS. 4-7 inclusive. As shown, a vein V is selected by the attending medical person for venipuncture and a percutaneous insertion of the entire needle and catheter tip is made on the patient. In this connection, the provision of the sharp bevel and the small diameter of the proximal tip gauge, combined with the remote or body bevel, serve to facilitate safe and easy needle insertion, as referred to in detail herein.

Referring now to preparation use, once the needle cover assembly 22 is removed, a sterile combination needle 10 and catheter 18 is available. The needle is then inserted into the vein with the first insertion being that of the tip 54 of the proximal gauge section 48. Subsequent movement of the assembly serves to embed the needle and catheter in the vein center, with the vein opening being thus enlarged sufficiently so as to accommodate the "Teflon" fluorocarbon catheter. When the insertion is complete, this fact is indicated by the appearance of blood in the viewing chamber 70 closed off by the microporous plug 14 in the remote end 72 of the needle hub 12. The microporous plug 72 permits passage of air from the needle interior and the chamber 70 so that fluid flashback can be observed in order that it can be substantially immediately determined that a proper needle insertion has been made. Thereafter, the catheter assembly 16 is fixed in relation to the patient while the needle assembly 10 is removed. A standard I.V. tubing male coupler (78 in FIG. 6) having standard intravenous tubing 80 affixed thereto is then moved into position and inserted in the counterbore 76 which had previously accommodated the microporous plug 14.

This completes the connection between an intravenous supply tube 80 and the catheter assembly 16, and the tubing 80 may be affixed as by tape 82 or the like to the patient as shown.

Referring now to FIG. 8, an alternative embodiment of the invention is shown. In FIG. 8, a needle tip portion generally designated 24a (and shown to have at its distal at the left side end as shown in FIG. 8) includes an exterior gauge surface 28a of a given diameter, a principal lumen 35a, extending axially therethrough and separated from the exterior or gauge surface 28a by a cylindrical sidewall 30a.

This needle tip 24a also includes a neckdown transition portion 46a of generally frustoconical form and extending from the exterior gauge surface 28a to a forward, reduced diameter gauge surface 48a. This gauge section terminates in a triple beveled tip point 54a. The tip element 24a is generally similar to that of its counterpart shown in FIG. 3a except that the tip is integrally formed as an extension of the needle tube, shown as 11a in FIG. 8.

According to the invention, there are some advantages to forming this needle as a single unit having a reduced diameter front gauge section to achieve the advantages of easier and more reliable insertion during venipuncture. Manufacturing units of this type may be accomplished by several methods. One such method involves simply cold drawing the tubular needle stock such as that from the which the body (11a in FIGS. 1–3a is made at its end portion to provide a reduced diameter nose section having a relatively smooth transition surface 46a. Thereupon, the triple beveled surface may be imparted to the needle body 11a to form the point 54a as shown in the drawings. In some cases, it may be necessary to anneal or otherwise treat the material to prevent excessive work hardening and to provide a surface suitable for finish manufacture. Drawing of the tubing may be accomplished with or without the aid of a mandrel or may otherwise be achieved as known to those skilled in the art.

Accordingly, while the invention may be advantageously practiced using a composite needle made from a separate needle tube element and a needle tip assembly, it may also be practiced by providing the same or similar shape in a one-piece, i.e., integrally formed needle.

While different materials may be suitable for use with the invention, depending on its intended application, a 304 stainless steel material is preferred for use in making the needle sleeve and the needle tip assembly. In one embodiment which has been found useful, the size of the lumen diameter 50 is 0.010 inches, that of the major or larger diameter lumen is 0.041 inches and the intermediate lumen 0.031. The tip body extension gauge 36 is 0.041 inches and the exterior diameter of the tip body 28 gauge and the needle sleeve gauge surface 28 are both 0.059 inches. The diameter of the proximal or tip gauge section 48 is 0.020 inches. This construction has been shown to provide excellent mechanical strength and stability. The attachment is done between the tip assembly and the sleeve portion of the needle has been accomplished by silver soldering. Independent testing laboratories have shown that needle and catheter assemblies made as described and utilizing silver solder for attachment of the needle tip to the sleeve pass the tissue toxicity (U.S.P. XXI, Biological Test—Plastics, pp. 1,235 and 1,236). These tests included extractions made with saline solution, alcohol, PEG and cottonseed oil.

It has also been discovered that manufacture at reasonable cost is facilitated by the nature and design of the separate tip assembly used in the two-piece form of the invention. This part may be made in automatic screw machines capable of counterboring of forming the exterior of the needle in the typical screw machine operation and boring the minor or lumen diameter through a relatively short plunge depth. Thereafter, the major lumen diameter is formed by counterboring and the larger diameter from the opposite end of the tip assembly. The smaller and larger gauge sections are then finished and the bevels are imparted to the needle prior to assemby thereof.

The needle is available in different sizes and is adaptable for use with different I.V. systems, although it is convenient to provided standard I.V. couplings (male and female sections) for attachment for standard intravenous tubing from which pharmocological fluids may be administered.

According to the invention, it has been discovered that ease of inserting the needle is accomplished without sacrificing essentially desirable characteristics of hypodermic needles. In patients who are elderly or in ill health, or wherein trauma has caused veinous constriction or collapse, it is nonetheless possible to make successful needle insertions using the very fine reduced diameter tip. The small diameter does not compromise the overall strength of the needle or its mechanical stability, since its entire length is not of such reduced diameter.

The ease and reliability of insertion is greatly improved and the likelihood that the vein will be traversed in the process of venipuncture, that is, that both near and far sides of the vein will be pierced by the needle with risk or further injury or at the least improper administration of fluids is substantially reduced or eliminated.

It will thus be seen that the present invention provides a novel hypodermic needle and methods of making them, which needles and methods have a number of advantages and characteristics, including those pointed out herein and other which are inherent in the invention.

Several preferred embodiments having been described by way of example, it is anticipated that various changes and modifications to the described form of apparatus may be made by those skilled in the art without departing from the spirit of the invention or the scope of the appended claims.

What is claimed is:

1. An improved hypodermic needle assembly for intravenous use in positioning a catheter within a vein, said needle assembly comprising, in combination, a principal needle portion and a proximal tip assembly portion, said principal needle portion comprising a cannula and means at the distal end of said cannula for attachment to a needle hub portion, said cannula having a proximal end opposite said distal end; a cylindrical exterior shank or gauge portion of a given diameter, a central bore or lumen portion of a given diameter and an annular end face at said proximal end of the cannula, said cannula at its proximal end receiving and positioning said proximal tip assembly portion, said tip assembly portion comprising a tip body having a first tip body gauge portion of substantially the same diameter as said gauge portion of said cannula, and a tip body rear extension, said rear extension having a gauge portion of a reduced diameter in relation to the diameter of said first body portion and a radial shoulder extending between said tip body rear extension and said first tip body gauge portion, said tip body shoulder engaging said proximal annular end face of said cannula, said tip assembly further including a major diameter passage or lumen extending through said rear extension gauge portion and at least a part of said tip body, with said tip assembly further including a generally frustoconical tip body bevel extending from said first tip body gauge portion, a proximal or exposed tip gauge portion of reduced diameter relative to the diameter of said cannula gauge portion extending from said body bevel, said tip assembly further including a pointed tip portion at the proximal end of said exposed tip gauge portion said pointed tip portion comprising a tip heel portion, a tip bevel and a pointed end said tip bevel extending between said pointed end and said tip heel portion, the proximal end of said tip body having a reduced diameter passage or lumen extending axially therethrough and communicating at its remote end with the interior of said major diameter lumen, the remote end of said reduced diameter lumen lying within said tip body, wherein a catheter is slidably receivable over said needle assembly such that a proximal end of the catheter is in substantially close proximity with said generally frustoconical tip body bevel, and whereby the proximal end of the catheter is adapted to be positioned within a vein when said tip body bevel is inserted into the same vein such that the catheter will remain in the vein when the needle assembly is removed from the vein.

2. A hypodermic needle as defined in claim 1 which further includes an indwelling catheter that is slidably received over said needle assembly and that covers said cannula gauge and at least a portion of said tip body to a location such that a proximal end of said indwelling catheter is closely positioned with respect to said generally frustoconical tip body bevel.

3. A hypodermic needle as defined in claim 1 wherein said tip bevel surface is a triple beveled surface.

4. A hypodermic needle as defined in claim 1 wherein the gauge diameter of said proximal or exposed tip gauge portion is not more than about 0.025 inch.

5. A hypodermic needle as defined in claim 1 wherein said first tip body gauge portion diameter is from about 0.015 to about 0.020 inch.

6. A hypodermic needle as defined in claim 1 wherein said distal end of said cannula includes a needle hub portion affixed thereto in fluid tight relation.

7. A hypodermic needle as defined in claim 1 further comprising a needle hub portion made from a translucent plastic material.

8. A hypodermic needle as defined in claim 1 further comprising a needle hub portion including counterbored axial passage and cylindrical bore portion receiving and positioning said distal end of said cannula, said needle hub portion further including a microporous plug adapted to be inserted into said counterbore, with said counterbore and said plug cooperating to provide a vented visible chamber in said needle hub portion to facilitate observing fluid flashback in said chamber when fluid flows into said chamber from said tip assembly.

9. An improved hypodermic needle assembly, said needle assembly comprising, in combination, a principal needle portion and a proximal tip portion, said principal needle portion comprising a cannula and means at the distal end of said cannula for attachment to a needle hub portion, said cannula having a proximal end opposite said distal end, a cylindrical exterior shank or gauge portion of a given diameter, and a central bore or lumen portion of a given diameter, said cannula terminating at its proximate end in a contoured proximal end portion, said contoured proximal end portion comprising a forward extendion of said cannula, said forward extension having substantially the same diameter as said gauge portion of said cannula, said forward extension of said proximal end portion including a major diameter passage or lumen extending axially therethrough and communicating with said lumen portion of said cannula, with said proximal end portion further including a generally frustoconical remote bevel portion extending from said forward extension, an exposed tip gauge portion of reduced diameter relative to the diameter of said cannula gauge portion extending from said remote bevel portion, said proximal end portion still further including a pointed tip portion at the proximal end of said exposed tip gauge portion, said pointed tip portion includes a tip heel portion and a tip bevel extending between the pointed tip and said tip heel portion, said proximal end portion having a reduced diameter lumen extending axially therethrough and communicating at its remote end with the interior of said major diameter passage or lumen, whereby a catheter is slidably receivable over said needle assembly such that a proximal end of such catheter is in substantially close proximity with said generally frustoconical remote bevel portion, and whereby the proximal end of the catheter is adapted to be positioned within a vein when said remote bevel portion is inserted into the same vein such that the catheter remains in the vein when the needle assembly is removed from the vein.

10. A hypodermic needle assembly as defined in claim 9 wherein the location of said communicating of the reduced diameter lumen with the major diameter lumen is closely spaced from said generally frustoconical remote bevel portion.

11. A hypodermic needle assembly as defined in claim 9 which further includes an indwelling catheter that is slidably received over said hypodermic needle assembly and that covers said cylindrical exterior shank and to a location such that a proximal end of said indwelling catheter is closely positioned with respect to said generally frustoconical remote bevel portion.

12. A hypodermic needle assembly as defined in claim 9 further comprising a hub portion including a counterbored axial passage and cylindrical bore portion receiving and positioning said distal end of said cannula, said needle hub portion further including a microporous plug adapted to be inserted into said counterbore, with said counterbore and said plug cooperating to provide a vented visible chamber in said needle hub portion to facilitate observing fluid flashback in said chamber when fluid flows into said chamber from said tip assembly.

* * * * *